United States Patent
Jaeger et al.

(10) Patent No.: US 9,388,118 B2
(45) Date of Patent: Jul. 12, 2016

(54) CONTINUOUS PROCESS FOR PREPARING (METH)ACRYLATES OF $C_{10}$-ALCOHOL MIXTURES

(71) Applicant: BASF SE, Ludwigshafen (DE)

(72) Inventors: Ulrich Jaeger, Roemerberg (DE); Volker Schliephake, Schifferstadt (DE); Ortmund Lang, Quirnbach (DE); Jochen Petzoldt, Basel (CH); Tobias Johannes Korn, Ludwigshafen (DE); Virginie Bette, Mannheim (DE); Claus Hechler, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 64 days.

(21) Appl. No.: 14/038,972

(22) Filed: Sep. 27, 2013

(65) Prior Publication Data

US 2014/0135523 A1    May 15, 2014

Related U.S. Application Data

(60) Provisional application No. 61/708,075, filed on Oct. 1, 2012.

(51) Int. Cl.
| | | |
|---|---|---|
| C07C 67/03 | (2006.01) | |
| C07C 67/08 | (2006.01) | |
| C07C 67/54 | (2006.01) | |
| C07C 69/52 | (2006.01) | |
| C07C 67/62 | (2006.01) | |

(52) U.S. Cl.
CPC ............... *C07C 67/62* (2013.01); *C07C 67/08* (2013.01); *C07C 67/54* (2013.01); *C07C 69/52* (2013.01)

(58) Field of Classification Search
CPC ........ C07C 67/03; C07C 69/52; C07C 67/08; C07C 67/54
USPC ........................................... 560/129, 205, 217
See application file for complete search history.

(56) References Cited

FOREIGN PATENT DOCUMENTS

| | | |
|---|---|---|
| DE | 100 36 879 A1 | 9/2001 |
| DE | 102 46 869 A1 | 3/2003 |
| DE | 10 2007 001 540 A1 | 8/2007 |
| EP | 2 257 519 | 12/2010 |
| WO | WO 98/56746 | 12/1998 |
| WO | WO 01/60779 A1 | 8/2001 |
| WO | WO-2009/106550 A1 * | 9/2009 .............. C07C 67/08 |
| WO | WO 2009/106550 A1 | 9/2009 |

OTHER PUBLICATIONS

U.S. Appl. No. 14/620,579, filed Feb. 12, 2015, Misske, et al.

* cited by examiner

*Primary Examiner* — Kamal Saeed
*Assistant Examiner* — Janet L Coppins
(74) *Attorney, Agent, or Firm* — Oblon, McClelland, Maier & Neustadt, L.L.P.

(57) ABSTRACT

A continuous process for preparing (meth)acrylates of $C_{10}$-alcohol mixtures by reaction of glacial (meth)acrylic acid with an isomer mixture of $C_{10}$-alcohols composed of 2-propylheptanol as the main isomer and at least one of the $C_{10}$-alcohols 2-propyl-4-methylhexanol, 2-propyl-5-methylhexanol, 2-isopropylheptanol, 2-isopropyl-4-methylhexanol, 2-isopropyl-5-methylhexanol and/or 2-propyl-4,4-dimethylpentanol, and the use of a diester of dicarboxylic acids which have been esterified with N-oxyl-containing compounds as polymerization inhibitors in such a process.

17 Claims, 1 Drawing Sheet

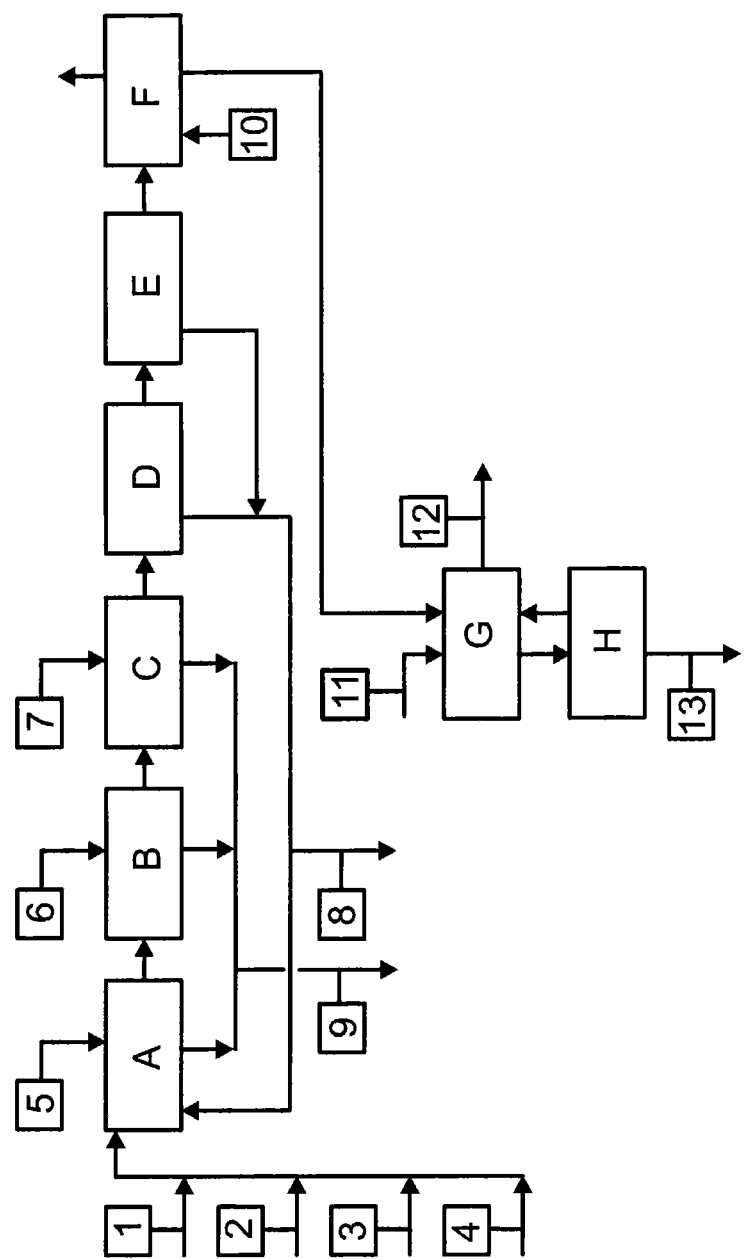

CONTINUOUS PROCESS FOR PREPARING (METH)ACRYLATES OF $C_{10}$-ALCOHOL MIXTURES

The invention relates to a continuous process for preparing (meth)acrylates of $C_{10}$-alcohol mixtures by esterification of (meth)acrylic acid with an isomer mixture of $C_{10}$-alcohols composed of 2-propylheptanol as the main isomer and at least one of the $C_{10}$-alcohols 2-propyl-4-methylhexanol, 2-propyl-5-methylhexanol, 2-isopropylheptanol, 2-isopropyl-4-methylhexanol, 2-isopropyl-5-methylhexanol and/or 2-propyl-4,4-dimethylpentanol The term "(meth)acrylic acid" in this document is an abbreviation of methacrylic acid and/or acrylic acid, "(meth)acrylic ester" an abbreviation of methacrylic ester and/or acrylic ester, and "(meth)acrylate" an abbreviation of methacrylate and/or acrylate.

The isomer mixture of $C_{10}$-alcohols consists of 2-propylheptanol as the main isomer and at least one of the $C_{10}$-alcohols 2-propyl-4-methylhexanol, 2-propyl-5-methylhexanol, 2-isopropylheptanol, 2-isopropyl-4-methylhexanol, 2-isopropyl-5-methylhexanol and/or 2-propyl-4,4-dimethylpentanol, these compounds, including 2-propylheptanol, being referred to hereinafter in abbreviated form as "propylheptanol isomers". The (meth)acrylates prepared therefrom are referred to in this document in abbreviated form as "propylheptyl (meth)acrylate".

The polymers and copolymers prepared on the basis of (meth)acrylates of propylheptanol isomers are of great economic significance in the form of polymer dispersions. They find use, for example, as adhesives, paints, or textile, leather and papermaking assistants.

DE 100 36 879 A1 already discloses a continuous process for preparing esters of (meth)acrylic acid by esterifying (meth)acrylic acid with $C_6$-$C_{10}$-alkanols.

The preparation of (meth)acrylates, especially 2-ethylhexyl acrylate, is likewise described in DE 102 46 869 A1.

WO 01/60779 A1 discloses the continuous preparation of (meth)acrylates of $C_6$-$C_{12}$-alkanols, cyclopentanol or cyclohexanol.

In addition, the batchwise preparation of (meth)acrylates of $C_{10}$-alcohol mixtures is described in EP 2 257 519 A1.

The continuous processes described in the prior art have the particular disadvantage that the multiple distillation of the target esters results in a particularly high energy expenditure, and the thermal stress can cause product losses and the formation of secondary components through decomposition of the target ester. In addition, the multiple heating leads to unwanted side reactions, for example polymerization.

It was accordingly an object of the invention to provide a process for preparing propylheptyl (meth)acrylates by direct esterification of (meth)acrylic acid with $C_{10}$-alcohol mixtures having 2-propylheptanol as the main isomer, which does not have the disadvantages of the prior art, and more particularly provides a high-quality target ester in an energetically favorable process.

The object was achieved by a continuous process for preparing (meth)acrylates of $C_{10}$-alcohol mixtures by reacting glacial (meth)acrylic acid with an isomer mixture of $C_{10}$-alcohols composed of 2-propylheptanol as the main isomer and at least one of the $C_{10}$-alcohols 2-propyl-4-methylhexanol, 2-propyl-5-methylhexanol, 2-isopropylheptanol, 2-isopropyl-4-methylhexanol, 2-isopropyl-5-methylhexanol and/or 2-propyl-4,4-dimethylpentanol, in the presence of at least one acidic catalyst and at least one polymerization inhibitor and in the presence of an azeotroping agent for the water of esterification, comprising the following process steps:

esterifying the glacial (meth)acrylic acid (1) with the isomer mixture of propylheptanol isomers (2) in the present of the acidic catalyst (3), the polymerization inhibitor (4) and the azeotroping agent for the water of esterification (5) in a reaction zone (A), the water of esterification being drawn off in a distillation zone connected atop the reaction zone (A) as an azeotrope with the azeotroping agent, giving a reaction output (process stage A), which is supplied to a neutralization, with neutralization of the acidic catalyst (3) and unconverted glacial (meth)acrylic acid (1) from the reaction output from the esterification by means of an alkaline solution to obtain crude propylheptyl (meth)acrylate (process stage B), washing the crude propylheptyl (meth)acrylate from process stage B to remove residues of salts from the crude propylheptyl (meth)acrylate (process stage C), azeotroping agents distillation of the washed crude propylheptyl (meth)acrylate from process stage C under reduced pressure and with continuous metered addition of at least one polymerization inhibitor, and drawing off the azeotroping agent, other low boilers and a very small proportion of propylheptyl (meth)acrylate (process stage D), low boiler removal from the bottom stream from process stage D under reduced pressure and with continuous metered addition of at least one polymerization inhibitor for removal of the residues of low boilers and of a small proportion of the propylheptyl (meth)acrylate (process stage E), air saturation of the bottom stream from process stage E in countercurrent by blowing in an oxygenous gas mixture and removing the resulting offgas (process stage F), purifying distillation of the bottom stream from process stage F under reduced pressure and with continuous metered addition of at least one polymerization inhibitor to obtain glacial propylheptyl (meth)acrylate and a bottom stream comprising the polymerization inhibitors and high boilers (process stage G);

residue distillation of the bottom stream from process stage G under reduced pressure and with continuous metered addition of at least one polymerization inhibitor, with separation of residual proportions of propylheptyl (meth)acrylate from polymerization inhibitors and high boilers (process stage H).

The process according to the invention is particularly advantageous compared to the known processes, since polymer was formed during the purifying distillation of the crude ester in the course of performance of the known procedure. The formation of the polymer can now be avoided by loading with an oxygenous gas (oxygen, air or lean air). This air saturation is described in detail below as process stage F.

The reactants from which the process according to the invention proceeds are of propylheptanol isomers and glacial (meth)acrylic acid.

In the present context, glacial (meth)acrylic acid refers to a (meth)acrylic acid quality comprising at least 98% by weight of (meth)acrylic acid or else with at least 99.5% by weight of (meth)acrylic acid, along with a maximum of 0.2% by weight of water and a maximum of 0.03% by weight each of acetic acid, propionic acid and isobutyric acid.

In the process according to the invention, a $C_{10}$-alcohol mixture comprising 2-propylheptanol as the main isomer is used. The term "main isomer" in the context of the present invention is understood to mean a content of 2-propylheptanol of up to 100% by weight, based on the total weight of the $C_{10}$-alcohol mixture. The 2-propylheptanol content is generally at least 50% by weight, preferably 60 to 98% by weight and more preferably 80 to 95% by weight, especially 85 to 95% by weight, based in each case on the total weight of the $C_{10}$-alcohol mixture.

As well as 2-propylheptanol as the main isomer, the $C_{10}$-alcohol mixture also comprises at least one of the $C_{10}$-alcohols 2-propyl-4-methylhexanol, 2-propyl-5-methylhexanol, 2-isopropylheptanol, 2-isopropyl-4-methylhexanol, 2-isopropyl-5-methylhexanol and/or 2-propyl-4,4-dimethylpentanol. These compounds, including 2-propylheptanol, are referred to in abbreviated form hereinafter as "propylheptanol isomers". The presence of other isomers of the 2-propylheptanol component—for example originating from the alcohols 2-ethyl-2,4-dimethylhexanol, 2-ethyl-2-methylheptanol and/or 2-ethyl-2,5-dimethylhexanol, which are isomers of 2-propylheptanol—in the $C_{10}$-alcohol mixture is possible, but these are present only in traces if at all.

Regarding preparation of 2-propylheptanol or propylheptanol isomers, reference is made here to German published specification DE 10 2007 001 540 A1 and the literature cited therein. Suitable mixtures of 2-propylheptanol with the isomeric alcohols thereof comprise, for example, those composed of 60 to 99% by weight of 2-propylheptanol, 0.1 to 15% by weight of 2-propyl-4-methylhexanol, 0.1 to 15% by weight of 2-propyl-5-methylhexanol and 0.01 to 5% by weight of 2-isopropylheptanol, the sum of the individual constituents not exceeding 100% by weight. The proportions of the individual constituents preferably add up to 100% by weight.

Preferred $C_{10}$-alcohol mixtures are, for example, those composed of 80 to 98% by weight of 2-propylheptanol, 0.5 to 10% by weight of 2-propyl-4-methylhexanol, 0.5 to 10% by weight of 2-propyl-5-methylhexanol and 0.1 to 2% by weight of 2-isopropylheptanol, the sum of the individual constituents not exceeding 100% by weight. The proportions of the individual constituents preferably add up to 100% by weight.

Particularly preferred $C_{10}$-alcohol mixtures are those composed of 90 to 95% by weight of 2-propylheptanol, 2 to 5% by weight of 2-propyl-4-methylhexanol, 2 to 5% by weight of 2-propyl-5-methylhexanol and 0.1 to 1% by weight of 2-isopropylheptanol, the sum of the individual constituents not exceeding 100% by weight. The proportions of the individual constituents preferably add up to 100% by weight.

Other $C_{10}$-alcohol mixtures which are likewise suitable are described in European patent application EP 2 257 519 A1, from page 3, line 30 to page 4, line 17.

The mixtures of 2-propylheptanol and the isomeric alcohols thereof may also comprise, as impurities, as a result of the preparation process, traces of n-pentanol, 2-methylbutanol and/or 3-methylbutanol. The contents of each of these alcohols are generally not more than 0.5% by weight, based on the total weight of the $C_{10}$-alcohol mixture.

The composition of the (meth)acrylates of $C_{10}$-alcohol mixtures which are prepared by the process according to the invention corresponds virtually to the composition of the propylheptanol isomer mixtures used in the esterification for preparation thereof.

The process according to the invention is advantageous since a high degree of esterification is achieved, and high yields are achieved in an energetically favorable process. Moreover, no significant polymer formation occurs.

The individual process stages are described hereinafter.

Esterification of the glacial (meth)acrylic acid with the isomer mixture of propylheptanol isomers (process stage A)

The reactants, glacial (meth)acrylic acid (1) and isomer mixture of propylheptanol isomers (2), are supplied continuously to a suitable reaction zone which may be either an individual reactor or a cascade of two or more reaction regions connected in series, in which case the output stream from one reaction region constitutes the feed stream for the next reaction region downstream. In the embodiment with a plurality of reaction regions, the ascending vapors from all reaction regions are preferably supplied to a single distillation unit, the liquid output of which is recycled only into the first reaction region.

The reaction units may be separate reactors or else different regions in one reactor.

The reactors used may be stirred tanks or kettles equipped with heating spirals or jackets, with an external natural circulation or forced circulation evaporator.

Connected atop the first reactor is a distillation column for the removal of the water of esterification.

Advantageously, the ascending vapors from all reaction regions can be supplied to a single distillation column, the output of which is supplied only to the first reaction region. However, it is also possible to equip all reaction vessels each with a dedicated distillation column connected on top.

The distillation column may be a column with random packing, a column with structured packing or a tray column, preferably with 1 to 15 theoretical plates.

Glacial (meth)acrylic acid and the isomer mixture of propylheptanol isomers are preferably used in a molar ratio in the range from 0.9 to 2.0, especially in the range from 1.05 to 1.15.

Suitable acidic esterification catalysts (3) are especially sulfuric acid, paratoluenesulfonic acid or other organic sulfonic acids, particularly methanesulfonic acid, benzenesulfonic acid or dodecylbenzenesulfonic acid.

The acid esterification catalyst is preferably supplied in a concentration of 1 to 5% by weight, based on the glacial (meth)acrylic acid used.

The azeotroping agent used for the water of esterification (5) is preferably a substance or a mixture of substances selected from the following list: cyclohexane, cyclohexene, methylcyclohexane, benzene, toluene, hexanes, hexenes, heptanes or heptenes, and derivatives thereof such as propylheptene.

The polymerization inhibitor (4) used is a substance or a mixture of substances in a concentration in the range from 100 to 5000 ppm, based on the output from the reaction zone, selected from the following list: phenothiazine, 4-nitrosophenol, 4-hydroxy-2,3,6,6-tetramethylpiperidine N-oxyl, hydroquinone or hydroquinone monomethyl ether. In a preferred variant of the process according to the invention, N-oxyl-containing stabilizers having a lower vapor pressure than the aforementioned stabilizers are used. These stabilizers are described in detail below.

Advantageously, oxygen can additionally be used as a polymerization inhibitor.

The reaction in process stage A is effected either under reduced pressure or under standard pressure, at a temperature between 70 and 140° C. (standard pressure), preferably between 100 and 130° C. (standard pressure). Preferably, the pressure and temperature range are the same in all reaction regions of the esterification (process stage A).

One or more distillation columns are connected on top of the reaction zone. The distillate obtained therein is condensed and separated in a phase separator into an organic phase and an aqueous phase. The aqueous phase is either added to the wastewater in need of treatment, or preferably sent to the wash in process stage C.

The organic phase comprising the azeotroping agent is returned as reflux to the distillation column(s) and optionally also directly to the reaction zone.

The esterification output from the reaction zone comprises the target ester, unconverted reactants, catalyst, polymerization inhibitor(s) and by-products.

Possible by-products include especially propylheptyl acetate, oxy esters of propylheptyl (meth)acrylate and propylheptanol isomers, esters of diacrylic acid with propylheptanol isomers, and propylheptyl propionate.

The esterification output is preferably cooled in a heat exchanger to a temperature of 20 to 40° C. and then sent to the neutralization (process stage B).

In general, the residence time in the esterification (process stage A) is between 5 and 30 hours, preferably between 5 and 15 hours.

Neutralization (Process Stage B)

In process stage B, the esterification output is freed of the catalyst and of unconverted (meth)acrylic acid with the aid of an alkaline solution, especially sodium hydroxide solution, potassium hydroxide solution or sodium carbonate.

The neutralization is preferably performed in mixer-settlers. The aqueous phase is sent to the wastewater in need of treatment, while the organic phase is sent to the next process stage, the wash (process stage C).

Wash (Process Stage C)

In this stage, the organic phase from the neutralization is freed of salts with the aid of a wash solution, especially water, which may advantageously be water from the phase separator of the reaction zone, i.e. process water. The aqueous phase is preferably sent to the wastewater in need of treatment. In apparatus terms, process stage C, like process stage B too, is performed in mixer-settlers. Useful settlers of the neutralization (process stage B) and also for the wash (process stage C) include, for example, decanters or extraction columns.

The washed crude ester (neutral ester) obtained in the wash is worked up in a series of distillation stages:

Azeotropic Disstillation (Process Stage D)

In the azeotropic disstillation, the azeotroping agent used in the reaction zone for removal of the water of esterification is distilled overhead and a large portion is preferably recycled into the esterification (process stage A). A small portion of the distillate is discharged to avoid accumulation of impurities.

Useful apparatus for the azeotropic disstillation include, for example, columns with random packing, columns with structured packing or tray columns having preferably 1 to 5 theoretical plates. The azeotropic disstillation is conducted preferably at a top pressure between 60 and 150 mbar, more preferably at a top pressure between 70 and 100 mbar.

Low Boiler Removal (Process Stage E)

In the low boiler removal, low boilers remaining are distilled out of the bottom product of the azeotropic disstillation overhead (process stage D) and preferably recycled into the neutralization (process stage B) or into the esterification (process stage A).

Useful apparatuses for the low boiler removal include, for example, columns with random packing, columns with structured packing or tray columns, preferably having 1 to 15 theoretical plates. The low boiler removal is preferably performed at a top pressure of 5 to 80 mbar, especially at a top pressure between 5 and 50 mbar.

It is possible to perform the azeotropic disstillation (process stage D) and the low boiler removal (process stage E) in a common distillation unit.

Air Saturation (Process Stage F)

In the air saturation, the crude product obtained from the bottom product of the low boiler removal (process stage E) is saturated in countercurrent by blowing in an oxygenous gas mixture. The oxygenous gas is preferably oxygen, air or what is called lean air. More preferably, the oxygen content of the oxygenous gas is between 1 and 21% by volume, more preferably between 4 and 8% by volume, based in each case on the total volume of the oxygenous gas.

The air saturation is effected at standard pressure or under a pressure which arises according to the amount of air introduced and the resulting pressure drop. The air saturation is effected in countercurrent, the air being introduced in countercurrent to the liquid comprising the crude product at a rate of 0.1 to 10 $m^3$/h, preferably of 0.5 to 5 $m^3$/h and more preferably of 1 to 2 $m^{g\ 3}$/h. These rate values are based on lean air with oxygen content approx. 6% by volume. If a gas mixture having a lower or higher oxygen content than lean air is to be used, the introduction rate has to be adjusted correspondingly in order to ensure sufficient saturation with oxygen in the liquid comprising the crude product.

The liquid comprising the crude product, under the given pressure (standard pressure) on introduction into the air saturation, has, for example, a temperature of 20 to 80° C., preferably of 30 to 50° C. This liquid comprising the crude product is introduced at a rate of, for example, 300 to 600 kg/h.

Useful apparatuses for the air saturation include, for example, columns with random packing, columns with structured packings or tray columns, preferably having 1 to 15 theoretical plates.

The liquid comprising the crude product is introduced at the top of the column, and the air is introduced into the lower part of the column. The air can be introduced through an inserted tube or through various distributor systems known to those skilled in the art. The liquid output from the bottom is—as described below—sent to the purifying distillation (process stage G).

Purifying Distillation (Process Stage G)

In the purifying distillation, the glacial propylheptyl (meth)acrylate is obtained in vaporous form from the bottom stream of the air saturation (process stage F) and stabilized with a storage stabilizer. Useful storage stabilizers include, for example, hydroquinone monomethyl ether.

Useful distillation apparatuses for the purifying distillation include, for example, columns with random packing, columns with structured packing or tray columns, especially having 1 to 15 theoretical plates, or else a thin-film evaporator. The purifying distillation is preferably conducted at a top pressure in the range from 1 to 20 mbar, more preferably at a top pressure in the range from 1 to 5 mbar.

Residue Distillation (Process Stage H)

In the residue distillation, proportions of the propylheptyl (meth)acrylate target ester still present are distilled out of the bottom product of the purifying distillation overhead and recycled into the purifying distillation. Useful apparatuses include columns with random packings, columns with structured packings or tray columns, especially having 1 to 15 theoretical plates, or else thin-film evaporators. The residue distillation is preferably performed at a top pressure in the range from 1 to 20 mbar, more preferably at a top pressure in the range from 1 to 5 mbar.

The purifying distillation (process stage G) affords glacial propylheptyl (meth)acrylate, glacial propylheptyl (meth)acrylate being understood in the present context to mean a glacial propylheptyl (meth)acrylate quality having at least 98% by weight of propylheptyl (meth)acrylate, not more than 1000 ppm of water, not more than 100 ppm of (meth)acrylic acid, a color number of <10 APHA, and 200 to 300+/−5 ppm of stabilizer, for example hydroquinone monomethyl ether.

Distillation apparatuses used in the individual distillation stages D to H each comprise an evaporator and a condensation unit. The evaporators may be natural circulation or forced circulation evaporators, falling-film evaporators or thin-film evaporators. Useful condensation units include, for example, shell-and-tube heat exchangers, plate heat exchangers or direct condensers (quench apparatuses).

In all process stages, polymerization inhibitors are added to counteract unwanted polymerization. Useful polymerization inhibitors include the above-described stabilizers or else mixtures thereof, for example phenothiazine, 4-nitrophenol, 4-hydroxy-2,2,6,6-tetramethylpiperidine N-oxyl, hydroquinone or hydroquinone monomethyl ether. These are generally used in a concentration of 100 to 5000 ppm based on the compound to be stabilized.

However, adverse effects have arisen in the case of use of 4-hydroxy-2,2,6,6-tetramethylpiperidine N-oxyl in the distillation, especially in the purifying distillation (process stage G). At the reduced pressure which is typically used therein at the top of the distillation unit of 1 to 20 mbar, preferably of 1 to 5 mbar, small amounts of this stabilizer are discharged together with the glacial propylheptyl (meth)acrylate via the top of the column. This can lead to adverse properties such as discoloration of the glacial propylheptyl (meth)acrylate and the polymers prepared therefrom. Especially in fields of application of such polymers in coatings, this is undesirable.

It has therefore been found that this disadvantage can be avoided if substances having the same mechanism of action, i.e. substances which likewise bear the stabilizing N-oxyl group, but having a higher molecular weight and hence low vapor pressure are used. As a result, especially high-quality target esters are obtained, since these are free of discoloring substances.

Such polymerization inhibitors comprise at least one N-oxyl group and have a vapor pressure of less than $10^{-5}$ mbar, preferably less than $10^{-6}$ mbar, more preferably less than $10^{-8}$ mbar and most preferably less than $5*10^{-9}$ mbar. Preferred polymerization inhibitors having at least one N-oxyl group and a low vapor pressure are esters of dicarboxylic acids. It is possible for only one acid group, but preferably both acid groups, of the dicarboxylic acid to have been esterified with the N-oxyl-containing compound.

Examples of suitable N-oxyl-containing compounds are 4-hydroxy-2,2,6,6-tetramethylpiperidine N-oxyl, 4-oxo-2,2,6,6-tetramethylpiperidine N-oxyl, 4-methoxy-2,2,6,6-tetramethylpiperidine N-oxyl, 4-acetoxy-2,2,6,6-tetramethylpiperidine N-oxyl, 2,2,6,6-tetramethylpiperidine N-oxyl, Uvinul® 4040P from BASF SE, 4,4',4"-tris(2,2,6,6-tetramethylpiperidine N-oxyl) phosphite, 3-oxo-2,2,5,5-tetramethylpyrrolidine N-oxyl, 1-oxyl-2,2,6,6-tetramethyl-4-methoxypiperidine, 1-oxyl-2,2,6,6-tetramethyl-4-trimethylsilyloxypiperidine, 1-oxyl-2,2,6,6-tetramethylpiperidin-4-yl 2-ethylhexanoate, 1-oxyl-2,2,6,6-tetramethylpiperidin-4-yl sebacate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl (4-tert-butyl)benzoate, bis(1-oxyl-2,2,6,6-tetramethylpiperidin-4-yl) succinate, bis(1-oxyl-2,2,6,6-tetrarnethylpiperidin-4-yl) adipate, bis(1-oxyl-2,2,6,6-tetramethylpiperidin-4-yl) 1,10-decanedioate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl)adipamide, N-(1-oxyl-2,2,6,6-tetramethylpiperidin-4-yl)caprolactam, N-(1-oxyl-2,2,6,6-tetramethylpiperidin-4-yl)dodecylsuccinimide, 2,4,6-tris-[N-butyl-N-(1-oxyl-2,2,6,6-tetramethylpiperidin-4-yl]triazine, N,N'-bis(1-oxyl-2,2,6,6-tetramethylpiperidin-4-yl)-N,N'-bis(formyl)-1,6-diaminohexane, 4,4'-ethylenebis(1-oxyl-2,2,6,6-tetramethylpiperazin-3-one).

Preferred N-oxyl-containing compounds are 4-hydroxy-2,2,6,6-tetramethylpiperidine N-oxyl, 4-oxo-2,2,6,6-tetramethylpiperidine N-oxyl, 4-methoxy-2,2,6,6-tetramethylpiperidine N-oxyl, 2,2,6,6-tetramethylpiperidine N-oxyl, 4-acetoxy-2,2,6,6-tetramethylpiperidine N-oxyl and 2,2,6,6-tetramethylpiperidine N-oxyl, particular preference being given to 4-hydroxy-2,2,6,6-tetramethylpiperidine N-oxyl.

Suitable dicarboxylic acids are all unbranched and branched carboxylic acids having two carboxylic acid groups, for example $C_2$-$C_{20}$-alkanedioic acids, in which, in the case of the unbranched dicarboxylic acids, the carboxylic acid groups may each be at the ends of the $C_1$-$C_{20}$-alkane chain. It will be appreciated that the carboxylic acid groups may also be anywhere in the alkane chain, in which case branched dicarboxylic acids are involved.

Preferred dicarboxylic acids are the unbranched saturated alkanedioic acids having a $C_2$-$C_{16}$-alkane chain, such as ethanedioic acid (oxalic acid), propanedioic acid (malonic acid), butanedioic acid (succinic acid), pentanedioic acid (glutaric acid), hexanedioic acid (adipic acid), heptanedioic acid (pimelic acid), octanedioic acid (cork acid, suberic acid), nonanedioic acid (azelaic acid), decanedioic acid (sebacic acid), undecanedioic acid, dodecanedioic acid, tridecanedioic acid (brassylic acid), tetradecanedioic acid and hexadecanedioic acid (thapsic acid). From this group, particular preference is given to the dicarboxylic acids having a $C_6$-$C_{14}$-alkane chain, and very particular preference to those having a $C_5$-$C_{12}$-alkane chain such as octanedioic acid (cork acid, suberic acid), nonanedioic acid (azelaic acid), decanedioic acid (sebacic acid), undecanedioic acid and dodecanedioic acid. Sebacic acid (decanedioic acid) is especially preferred.

It will be appreciated that these alkanedioic acids may also be mono- or polyunsaturated, for example maleic acid or fumaric acid. Likewise useful are mono- or polysubstituted alkanedioic acids, for example hydroxy-substituted alkanedioic acids (tartronic acid, tartaric acid, maleic acid), keto-substituted alkanedioic acids (a-ketoglutaric acid, oxaloacetic acid) and amino-substituted alkanedioic acids (glutamic acids, aspartic acid). In the case of unsaturated alkanedioic acids, these may also be present as an aromatic ring, for example phthalic acid, isophthalic acid and terephthalic acid.

The dicarboxylic acid and the N-oxyl-containing compound are selected by the person skilled in the art such that the diester of the dicarboxylic acid with the N-oxyl groups has a vapor pressure of less than $10^{-5}$ mbar, preferably less than $10^{-6}$ mbar, more preferably less than $10^{-8}$ mbar and most preferably less than $5*10^{-9}$ mbar.

A particularly preferred representative of the substance class is the diester of sebacic acid the 4-hydroxy-2,2,6,6-tetramethylpiperidine N-oxyl, which is also available under the Prostab® 5415 trade name from BASF SE.

In the case of use of those diesters of dicarboxylic acids which have been esterified with N-oxyl-containing compounds, it was possible to detect less than 20 ppm, preferably less than 10 ppm and more preferably less than 5 ppm of the N-oxyl compound in the glacial propylheptyl (meth)acrylate.

All of the above-described polymerization inhibitors, i.e. phenothiazine, 4-nitrophenol, 4-hydroxy-2,2,6,6-tetramethylpiperidine N-oxyl, hydroquinone or hydroquinone monomethyl ether, and the diesters of dicarboxylic acids which have been esterified with N-oxyl-containing compounds, can be metered in alone or in any desired mixture, either in solid form or as solution. They are preferably supplied as a solution.

A useful solvent here for the polymerization inhibitor(s) is glacial propylheptyl (meth)acrylate, but also the corresponding crude ester or washed crude ester (neutral ester). The concentration of polymerization inhibitor in the solution is between 0.1 and 2.0% by weight. This solution is preferably run directly to the respective distillation columns, for example via a return line or the condensers at the top of the column.

The vacuum in the individual distillation columns can be generated by means of steam ejectors or liquid ring pumps which are operated, for example, with water.

The residues from the azeotropic distillation and from the residue distillation can be thermally utilized, for example, in a suitable incineration plant. The offgases coming from the plant can be disposed of, for example, in a flare.

The invention is illustrated in detail hereinafter with reference to a drawing and a working example.

FIG. 1 shows the schematic diagram of a preferred plant for performing the process according to the invention.

In the sole FIGURE, process stages A to H are indicated by arrows which symbolize streams. The large arrows symbolize the main stream to the target ester, the glacial propylheptyl (meth)acrylate.

A stream 1 comprising glacial (meth)acrylic acid, a stream 2 comprising propylheptanol isomers, a stream 3 comprising acidic catalyst, a stream 4 comprising polymerization inhibitor and a stream 5 comprising azeotroping agent are supplied to process stage A, the esterification.

The main stream from process stage A is passed into process stage B, the neutralization, in which a neutralization is effected with addition of an alkali solution, stream 6. The main stream from the neutralization is passed into process stage C, the wash, in which a wash solution, stream 7, is supplied to obtain a washed crude ester, which is subsequently passed into process stage D, the azeotropic distillation. From the azeotropic distillation, an azeotroping agent-comprising stream can be recycled into process stage A, the esterification. The main stream from the azeotropic distillation is passed into process stage E, the lower boiler removal. From this, a substream, optionally together with the substream from the azeotropic distillation, can be recycled into process stage A, the esterification. The main stream from the low boiler removal, process stage E, is passed into the air saturation, process stage F, in which an oxygenous gas, stream 10, is passed through in countercurrent. The bottom stream from the air saturation is passed into the purifying distillation, process stage G. Process stage G is supplied with a stabilizer, stream 11, and the target ester, glacial propylheptyl (meth)acrylate, stream 12, is drawn off in vaporous form. The bottom stream from the purifying distillation is worked up further in a residue distillation, process stage G, from which a high boiler residue, stream 13, is discharged.

The present invention further provides for the use of said diesters of dicarboxylic acids in which both acid groups of the dicarboxylic acid have been esterified with an N-oxyl-containing compound as polymerization stabilizers in a distillative or rectificative purification of (meth)acrylic esters having a boiling point (at standard pressure) of >150° C., preferably of >180° C., more preferably of >200° C. and most preferably of >220° C. Such (meth)acrylic esters are, for example, 2-propylheptyl (meth)acrylate, hydroxyalkyl (meth)acrylates such as 2-hydroxyethyl (meth)acrylate and 4-hydroxybutyl (meth)acrylate, cyclohexyl (meth)acrylate and (meth)acrylates of fatty alcohols having 12 to 18 carbon atoms and of mixtures of these fatty alcohols, for example a mixture of fatty alcohols having a $C_{16}$- and $C_{18}$-alkyl chain, having a $C_{13}$- and $C_{15}$-alkyl chain, or having a $C_{12}$- and $C_{14}$-alkyl chain. Examples of such (meth)acrylates of fatty alcohols are lauryl (meth)acrylate, cetyl (meth)acrylate and stearyl (meth)acrylate.

In the case of use of such diesters of dicarboxylic acids which have been esterified with N-oxyl-containing compounds, less than 20 ppm, preferably less than 10 ppm and more preferably less than 5 ppm of the N-oxyl compound can be detected in the glacial ester. As a result, especially high-quality target esters are obtained, since these are free of discoloring substances.

EXAMPLES

Example 1

Preparation of 2-propylheptyl Acrylate with Air Saturation (Process Stage F)

In a process for continuously preparing propylheptyl acrylate, 111 kg/h of acrylic acid having a content of phenothiazine as a process stabilizer of 0.1% by weight, based on the weight of the acrylic acid, 2 kg/h of a 65% aqueous solution of methanesulfonic acid and 210 kg/h of propylheptanol isomers were metered continuously into the first reactor of a three-stage reactor cascade with natural circulation evaporators. The reactants each corresponded to the quality specified below, the components being specified in % by weight:

Acrylic acid with 99.5% acrylic acid, 0.1% water, 0.13% diacrylic acid and 0.12% acetic acid, propylheptanol isomers with 93% 2-propylheptanol, 2.9% 2-propyl-4-methylhexanol, 3.9% 2-propyl-5-methylhexanol and 0.2% isopropylheptanol.

Additionally supplied continuously to the first reactor of the cascade was a circulation stream from the top of the azeotropic distillation (process stage D) of 130 kg/h having the following composition: 22.57% by weight of cyclohexane, 8.16% by weight of propylheptanol isomers, 66.77% by weight of propylheptyl acrylate and 1.36% by weight of acrylic acid.

The distillation column which was connected on top of the first reactor of the cascade was supplied with 185 kg/h of cyclohexane as an azeotroping agent for removal of the water of esterification as a return stream.

The molar methacrylic acid/propylheptanol isomer ratio in the reactor feed was 1.16:1.

In the reactors of the cascade, a temperature of 120° C. was established.

From the third reactor of the cascade, a reaction output of 598 kg/h was drawn off with the following specified composition: 10% by weight of cyclohexane, 2% by weight of propylheptanol isomers, 83.8% by weight of propylheptyl acrylate, 2.1% by weight of acrylic acid and 0.65% by weight of methanesulfonic acid.

The reactor output was cooled to a temperature of 30° C. and neutralized with a 20% aqueous sodium carbonate solution in process stage B. The molar ratio of sodium carbonate to acrylic acid+methanesulfonic acid was 3.5:1.

The neutral ester obtained in process stage B was freed of residual salts and washed in process stage C with 1200 kg/h of water in a mixer-settler apparatus. The washed neutral ester was sent to process stage D, the azeotropic distillation. The cyclohexane-enriched distillate was supplied to the boiler of the first esterification reactor.

The azeotropic distillation was performed at a top pressure of 60 mbar and a bottom temperature of 85° C. in a rectification column equipped with size 35 Pall rings.

The bottoms discharge from the azeotropic distillation was distilled in process stage E, the low boiler removal, at a top pressure of 15 mbar and a bottom temperature of 140° C. in a distillation column equipped with size 25 Pall rings.

The distillate which comprised, aside from the propylheptanol isomers, principally propylheptyl acrylate was recycled into the first reactor of the esterification cascade. Optionally, a portion of the low boilers could have been discharged.

In process stage F, the air saturation, the crude ester obtained from the low boiler removal (process stage E) was contacted with lean air in countercurrent. For this purpose, 330 kg/h of crude ester were introduced at the top of a column equipped with size 25 Pall rings. In the lower part of the column, 1 m³/h of lean air having an oxygen content of 6% by volume was introduced. The temperature in the column was 25° C.

In process stage G, the purifying distillation, in a first thin-film evaporator at an evaporation ratio (ratio of vapor stream to feed stream) of about 75%, a top stream of 275 kg/h of glacial propylheptyl acrylate having the following composition was obtained:

99.39% by weight of propylheptyl acrylate, 0.16% by weight of propylheptyl acetate, 0.11% by weight of propylheptyl diacrylate and 0.22% by weight of propylheptanol. The glacial propylheptyl acrylate was stabilized against polymerization for storage by addition of hydroquinone monomethyl ether (MEHQ) in a concentration of 250 ppm.

Example 2

Examples for Stabilization of the Purifying Distillation (Process Stage G) of Propylheptyl Acrylate Examples 2a to 2c below were performed analogously to example 1.

Example 2a (Comparative Example)

Purifying Distillation of Propylheptyl Acrylate with PTZ/MEHQ Without Air Saturation (Process Stage F)

367 kg/h of crude propylheptyl acrylate from the low boiler removal (process stage E) were stabilized with phenothiazine (PTZ) and hydroquinone monomethyl ether (MEHQ) to a content of 200 ppm of PTZ and 200 ppm of MEHQ. The distillation in the thin-film evaporator was performed at a top pressure of 96° C. and a top pressure of 5 mbar. 275 kg/h of glacial propylheptyl acrylate were obtained. After about 20 hours, polymerization set in; the distillation unit had to be shut down and cleaned.

Example 2b

Purifying Distillation of Propylheptyl Acrylate with PTZ/MEHQ with Air Saturation (Process Stage F)

367 kg/h of crude propylheptyl acrylate from the air saturation (process stage F) were stabilized with PTZ and MEHQ to a content of 200 ppm of PTZ and 200 ppm of MEHQ. The distillation in the thin-film evaporator was performed at a top temperature of 99° C. and a top pressure of 6 mbar. 275 kg/h of glacial propylheptyl acrylate were obtained. The distillation ran for 48 hours without polymerization in the distillation unit. A portion of the MEHQ stabilizer goes overhead in the pure product in the course of distillation owing to the volatility thereof (vapor pressure approx. 1.4 Pa at 25° C., approx. 370 Pa at 100° C.). The dosage of the MEHQ stabilizer into the crude propylheptyl acrylate is thus difficult to set since portions thereof are distilled as well.

Example 2c

Purifying Distillation of Propylheptyl Acrylate with PTZ/Prostab® 5415 with Air Saturation 356 kg/h of crude propylheptyl acrylate from the air saturation (process stage F) were stabilized with PTZ and a diester of sebacic acid and 4-hydroxy-2,2,6,6-tetramethylpiperidine N-oxyl (obtainable under the Prostab® 5415 trade name from BASF SE) to a content of 200 ppm of PTZ and 200 ppm of Prostab® 5415. The distillation in the thin-film evaporator was performed at a top temperature of 99° C. and a top pressure of 6 mbar. 275 kg/h of glacial propylheptyl acrylate were obtained. The distillation ran for >96 hours without polymerization in the distillation unit. No N-oxyl compounds were detectable in the glacial propylheptyl acrylate.

Example 3

Examples for Stabilization of the Purifying Distillation (Process Stage G) of 4-hydroxybutyl Acrylate (4-HBA)

Propylheptyl acrylate and 4-HBA have similar boiling points (propylheptyl acrylate: 250° C. at $10^5$ Pa, 4-HBA: 230° C. at $10^5$ Pa). To improve the stability, 4-hydroxy-2,2,6,6-tetramethylpiperidine N-oxyl (HOT) was used rather than MEHQ during the purifying distillation (process stage G).

Examples 3a and 3b which follow were otherwise performed analogously to example 1.

Example 3a (Comparative Example)

Purifying Distillation of 4-HBA with PTZ/HOT with Air Saturation (Process Stage F)

367 kg/h of crude 4-hydroxybutyl acrylate from the air saturation (process stage F) were stabilized with PTZ and HOT to a content of 200 ppm of PTZ and 200 ppm of HOT. The distillation in the thin-film evaporator was performed at a top temperature of 102° C. and a top pressure of 5 mbar. 280 kg/h of pure 4-hydroxybutyl acrylate were obtained. The distillation ran for >96 hours without polymerization in the distillation unit. In the glacial 4-hydroxybutyl acrylate, up to 65 ppm of the N-oxyl compound were detected. However, this is undesirable in the 4-HBA since it can lead to discoloration in polymers comprising 4-HBA. Such discolorations are undesirable particularly in the coatings sector.

Example 3b

Purifying distillation of 4-HBA with PTZ/Prostab® 5415 with air saturation (process stage F)

356 kg/h of crude 4-hydroxybutyl acrylate from the air saturation (process stage F) were stabilized with PTZ and a diester of sebacic acid and 4-hydroxy-2,2,6,6-tetramethylpiperidine N-oxyl (obtainable under the Prostab® 5415 trade name from BASF SE) to a content of 200 ppm of PTZ and 200 ppm of Prostab® 5415. The distillation in the thin-film evaporator was performed at a top temperature of 102° C. and a top pressure of 5 mbar. 270 kg/h of glacial 4-hydroxybutyl acrylate were obtained. The distillation ran for >96 hours without polymerization in the distillation unit. In the glacial 4-hydroxybutyl acrylate, no N-oxyl compounds were detectable.

The invention claimed is:

1. A continuous process for preparing (meth)acrylates of $C_{10}$-alcohol mixtures, the process comprising:
   (A) esterifying, in a reaction zone, glacial (meth)acrylic acid with an isomer mixture of propyheptanol isomers in the presence of a acidic catalyst, at least one polymerization inhibitor and an azeotroping agent for the water of esterification, such that the water of esterification is drawn off in a distillation zone connected atop the reaction zone as an azeotrope with the azeotroping agent, to obtain a reaction output;

(B) neutralizing the acidic catalyst and unconverted glacial (meth)acrylic acid in the reaction output with an alkaline solution to obtain a crude propylheptyl (meth)acrylate;

(C) washing the crude propylheptyl (meth)acrylate to remove residues of salts from the crude propylheptyl (meth)acrylate, to obtain a washed crude propylheptyl (meth)acrylate;

(D) distilling the washed crude propytheptyl (meth)acrylate under reduced pressure and with continuous metered addition of at least one polymerization inhibitor, while drawing off the azeotroping agent, other low boilers and a very small proportion of propylheptyl (meth)acrylate;

(E) removing low boilers from a bottom stream of the distillation (D) under reduced pressure and with continuous metered addition of at least one polymerization inhibitor to remove residues of low boilers and a small proportion of the propylheptyl (meth)acrylate;

(F) air saturating the bottom stream in countercurrent by blowing in an oxygenous gas mixture and removing a resulting offgas, to form a resulting bottom stream;

(G) distilling the resulting bottom stream under reduced pressure and with continuous metered addition of at least one polymerization inhibitor to obtain glacial propylheptyl (meth)acrylate and a further bottom stream comprising polymerization inhibitors and high boilers;

(H) distilling the further bottom stream under reduced pressure and with continuous metered addition of at least one polymerization inhibitor, with separation of residual propylheptyl (meth)acrylate from polymerization inhibitors and high boilers, to obtain (meth)acrylates of $C_{10}$ alcohol mixtures, wherein the isomer mixture of propylheptanol isomers comprises 2-propylheptanol as the main isomer and at least one of the 2-propyl-4-methythexanol, 2-propyl-5-methylhexanol, 2-isopropylheptanol, 2-isopropyl-4-methylhexanot, 2-isopropyi-5-methylhexanol and 2-propyl-4,4-dimethylpentanot.

2. The process according claim 1, wherein the oxygenous gas is oxygen, air or lean air.

3. The process according to claim 2, wherein an oxygen content of the oxygenous gas is between 1 and 21% by volume, based on a total volume of the oxygenous gas.

4. The process according to claim 2, wherein an oxygen content of the oxygenous gas is between 4 and 8% by volume, based on a total volume of the oxygenous gas.

5. The process according to claim 1, wherein air in the air saturation (F) is introduced in countercurrent to a liquid comprising crude product at a rate of 0.1 to 10 m³/h, based on lean air having an oxygen content of about 6% by volume.

6. The process according to claim 5, wherein the air is introduced in countercurrent to the liquid comprising the crude product at a rate of 0.5 to 5 m³/h, based on lean air having oxygen content of about 6% by volume.

7. The process according to claim 1, wherein a liquid comprising crude product is introduced in the air saturation (F) at a rate of 300 to 600 kg/h.

8. The process according to claim 1, wherein the air saturating (F) occurs in an apparatus comprising a column with random packing, a column with structured packing or a tray column.

9. The process according to claim 1, wherein the at least one polymerization inhibitor is selected from the group consisting of phenothiazine, 4-nitrosophenol, 4-hydroxy-2,2,6,6-tetramethylpiperdine N-oxyl, hydroquinone, hydroquinone monomethyl ether, and a diester of a dicarboxylic acid which has been esterified with an N-oxyl-containing compound.

10. The process according to claim 9, wherein the at least one polymerization inhibitor is a diester of a dicarboxylic acid which has been esterified with at least one N-oxyl-containing compound and has a vapor pressure of less than $10^{-5}$ mbar.

11. The process according claim 9, wherein the diester has a vapor pressure of less than $10^{-6}$ mbar.

12. The process according to claim 9, wherein the at least one polymerization inhibitor is a diester of a dicarboxylic acid which has been esterified with 4-hydroxy-2,2,6,6-tetramethylpiperdine N-oxyl.

13. The process according to claim 9, wherein the at least one polymerization inhibitor is a diester of sebacic acid which has been esterified with 4-hydroxy-2,2,6,6-tetramethylpiperidine N-oxyl.

14. A process for inhibiting polymerization in a distillative or rectificative purification of (meth)acrylic esters, the process comprising adding a diester of a dicarboxylic acid, which has been esterified with an N-oxyl-containing compound and has a vapor pressure of less than $10^{-5}$ mbar, to a distillative or rectificative purification of a (meth)acrylic ester having a boiling point (at standard pressure) of greater than 150° C.

15. The process according to claim 14, wherein the (meth)acrylic ester is selected from the group consisting of propylheptyl (meth)acrylate, a hydroxyalkyl (meth)acrylate, cyclohexyl (meth)acrylate, a (meth)acrylate of a fatty alcohol having 12 to 18 carbon atoms, and mixtures thereof.

16. The process according to claim 14, wherein the (meth)acrylic ester is 2-hydroxyethyl (meth)acrylate or 4-hydroxybutyl (meth)acrylate.

17. The process according to claim 14, wherein the diester has a vapor pressure of less than $10^{-6}$ mbar.

* * * * *